United States Patent [19]
Granger et al.

[11] Patent Number: 5,569,301
[45] Date of Patent: Oct. 29, 1996

[54] SURGICAL INCISION MEMBERS FOR ENDOSCOPIC SUTURING APPARATUS

[75] Inventors: Richard N. Granger; Paul A. Scirica, both of Huntington; Michael J. Gorecki, Cromwell, all of Conn.

[73] Assignee: United States Surgical Corporation, Norwalk, Conn.

[21] Appl. No.: 260,579

[22] Filed: Jun. 16, 1994

Related U.S. Application Data

[63] Continuation-in-part of Ser. No. 134,145, Oct. 8, 1993, abandoned.

[51] Int. Cl.⁶ .................................................. A61B 17/04
[52] U.S. Cl. ........................... 606/224; 606/223; 606/225
[58] Field of Search .................................... 606/222–227, 606/139, 147; 112/222–224

[56] References Cited

U.S. PATENT DOCUMENTS

| | | |
|---|---|---|
| 1,037,864 | 9/1912 | Carlson et al. . |
| 2,516,710 | 7/1950 | Mascolo . |
| 2,910,983 | 11/1959 | Everett . |
| 3,090,386 | 5/1963 | Curtis . |
| 3,349,772 | 10/1967 | Rygg . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer ........................ 128/334 R |
| 4,120,255 | 10/1978 | McLain . |
| 4,159,686 | 7/1979 | Heim . |
| 4,194,457 | 3/1980 | Parsons . |
| 4,195,584 | 4/1980 | Falk et al. . |
| 4,236,470 | 12/1980 | Stenson . |
| 4,248,165 | 2/1981 | Addy et al. . |
| 4,316,562 | 2/1982 | Davidson et al. . |
| 4,327,655 | 5/1982 | Addy et al. . |
| 4,345,601 | 8/1982 | Fukuda . |
| 4,458,614 | 7/1984 | Iwashita . |
| 4,527,564 | 7/1985 | Eguchi et al. . |
| 4,781,190 | 11/1988 | Lee .......................................... 606/139 |
| 5,180,385 | 1/1993 | Sontag . |
| 5,193,473 | 3/1993 | Asao et al. . |
| 5,224,955 | 7/1993 | West . |
| 5,250,053 | 10/1993 | Snyder . |

FOREIGN PATENT DOCUMENTS

| | | |
|---|---|---|
| 0 601 676 A2 | 6/1994 | European Pat. Off. . |
| 41 24 383 C1 | 5/1992 | Germany . |
| 41 24 381 C1 | 8/1992 | Germany . |
| 41 39 628 C1 | 3/1993 | Germany . |
| 1725847-A1 | 4/1992 | U.S.S.R. . |
| 9215252 | 3/1992 | WIPO . |
| WO93/01750 | 2/1993 | WIPO . |

OTHER PUBLICATIONS

Aesculap Catalog, p. 401 (Date: 1905).

*Primary Examiner*—Gary Jackson

[57] ABSTRACT

A surgical incision member is provided including a body portion defining first and second longitudinal ends, tissue penetrating portion adjacent each longitudinal end of the body portion, suture attachment structure intermediate the tissue penetrating portions, and a suture attached to the suture attachment structure. A method is also provided wherein the suture is attached to the surgical incision member by adhesives or by crimping.

16 Claims, 7 Drawing Sheets

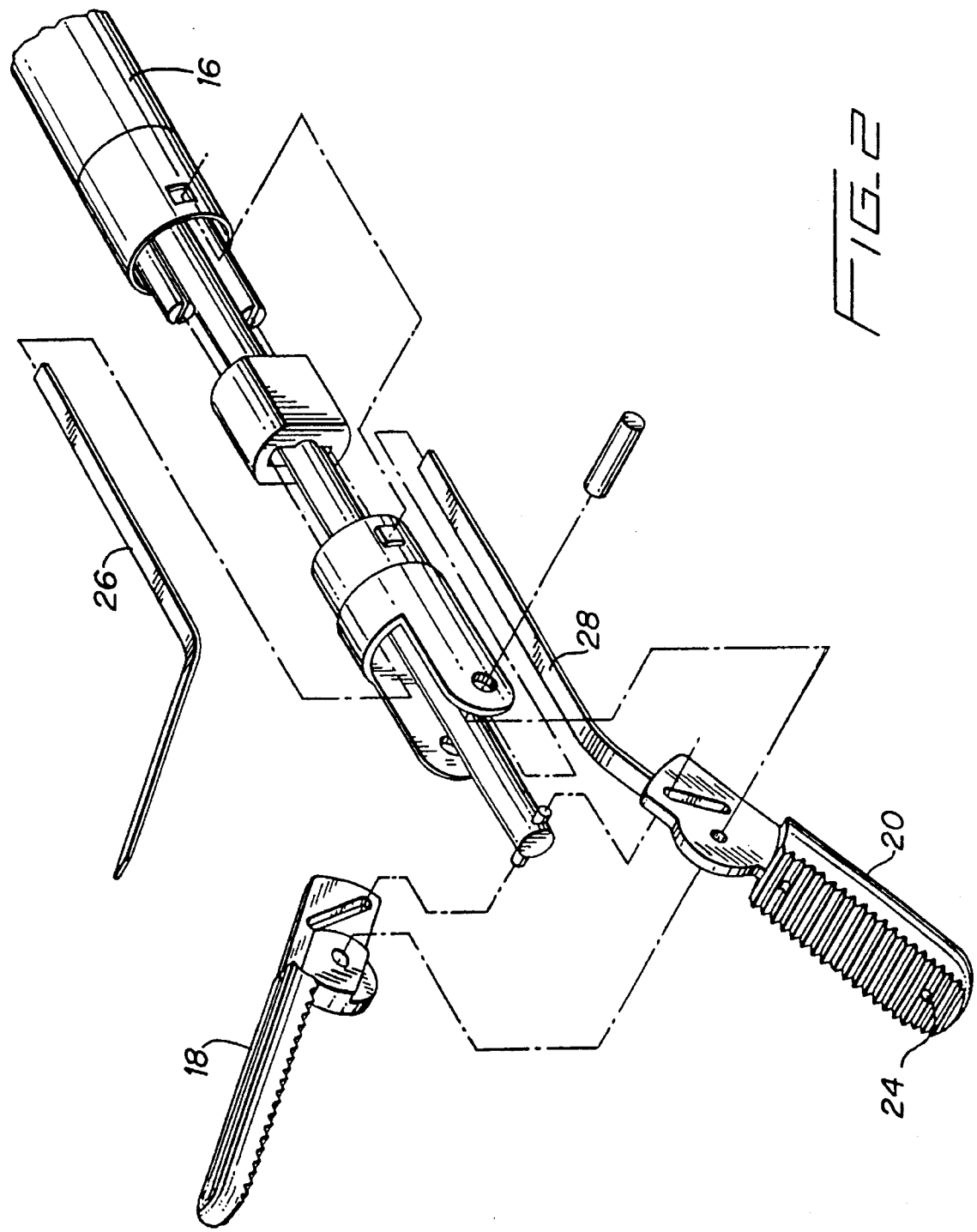

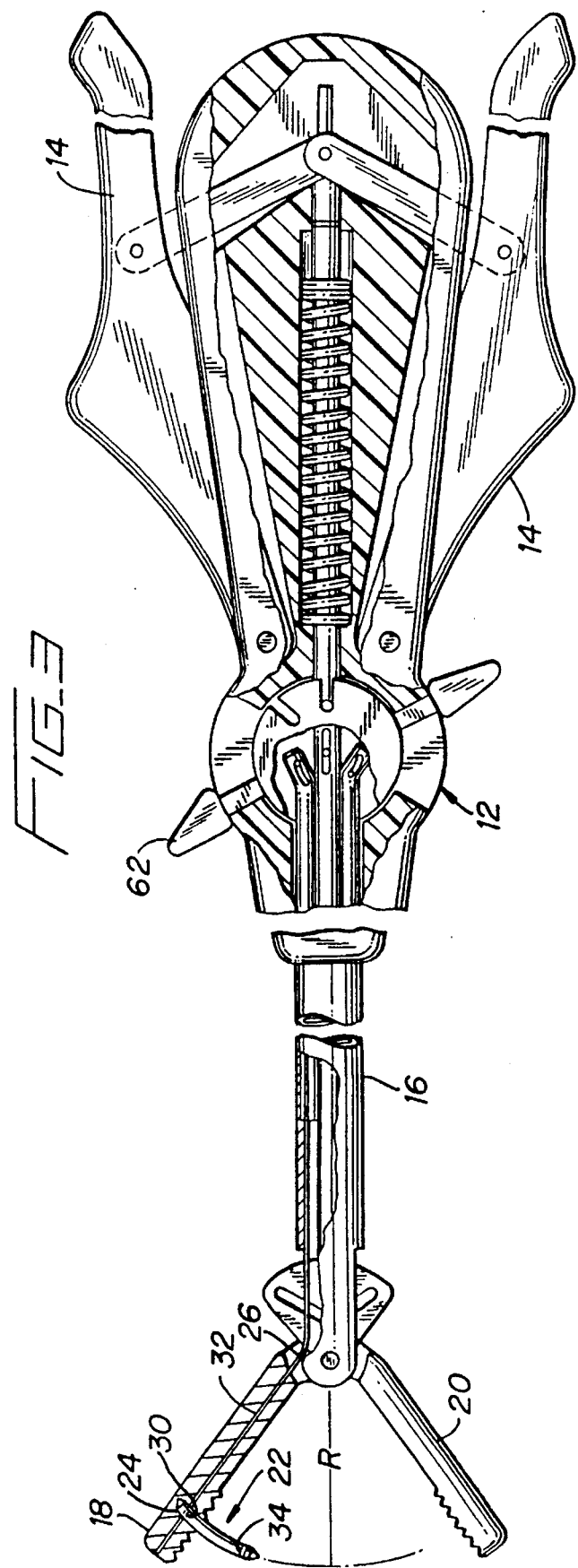

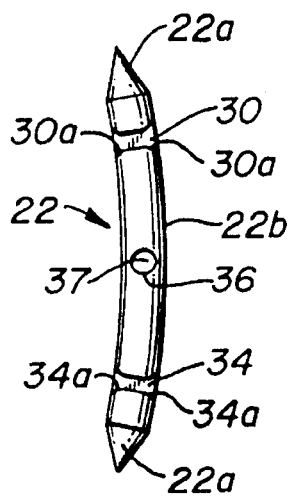
FIG_4
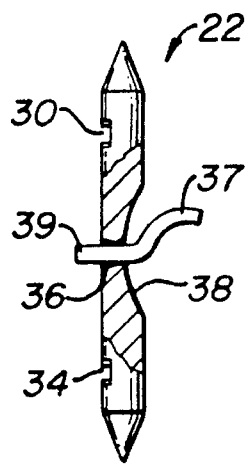
FIG_5
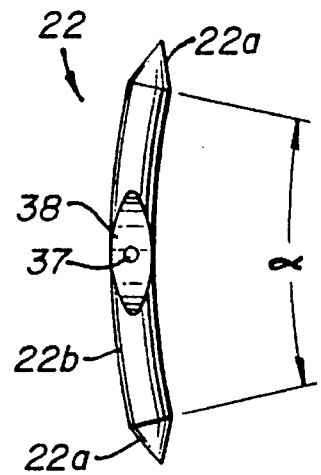
FIG_6
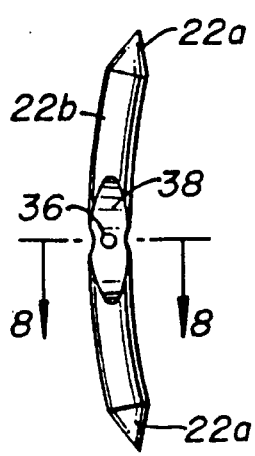
FIG_7
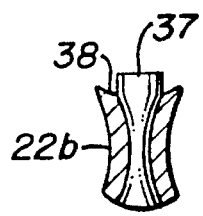
FIG_8
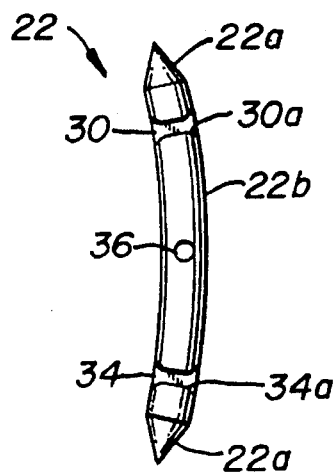
FIG_9

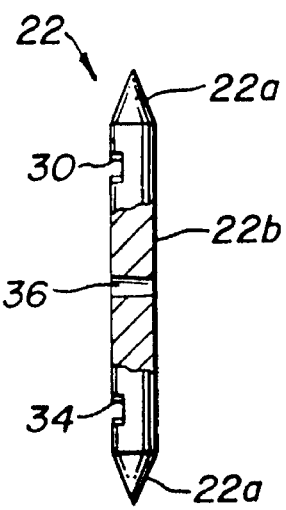
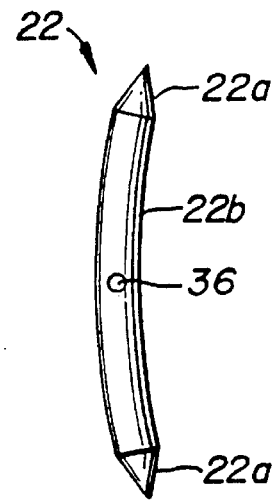
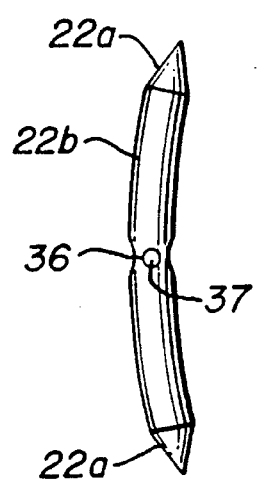
FIG_10        FIG_11        FIG_12
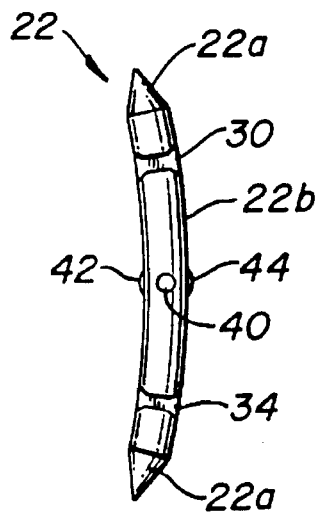
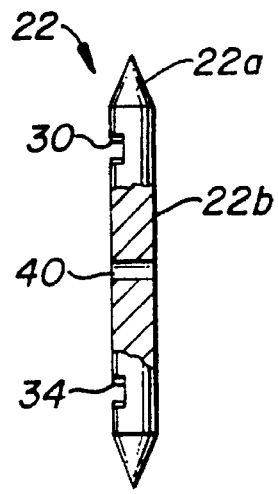
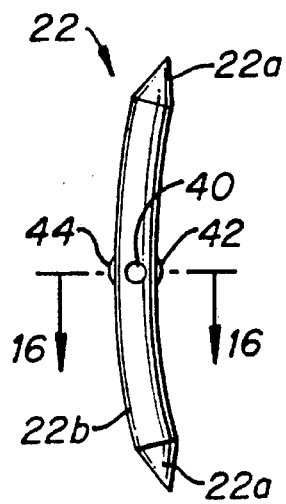
FIG_13        FIG_14        FIG_15

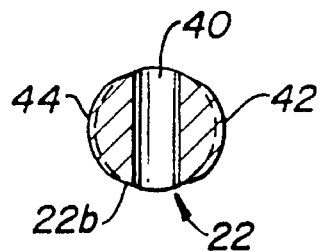
FIG_16
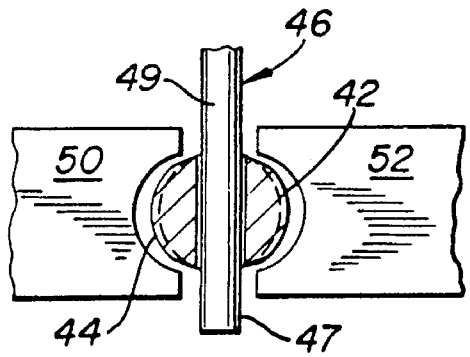
FIG_17
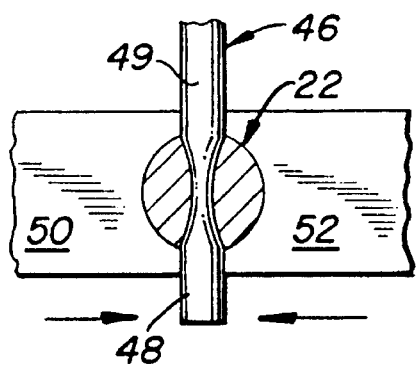
FIG_18
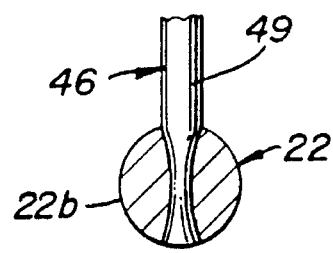
FIG_19
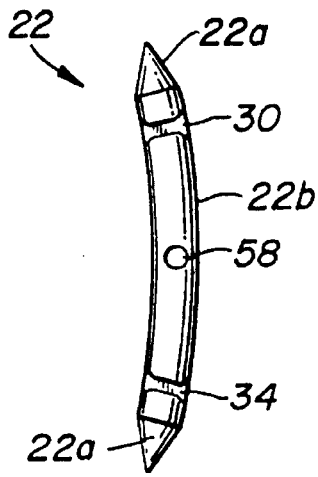
FIG_20
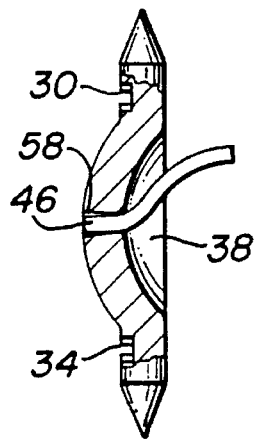
FIG_21
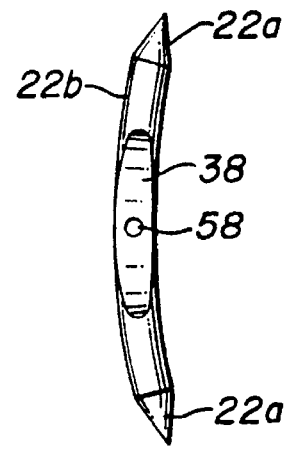
FIG_22

SURGICAL INCISION MEMBERS FOR ENDOSCOPIC SUTURING APPARATUS

CROSS REFERENCE TO RELATED APPLICATIONS

This application is a continuation-in-part of copending Application Ser. No. 08/134,145, filed on Oct. 8, 1993 now abandoned.

BACKGROUND

1. Technical Field

This application relates generally to surgical incision instrumentation and, more particularly to surgical incision members used in conjunction with endoscopic or laparoscopic suturing apparatus.

2. Description of Related Art

Endoscopic or laparoscopic procedures are characterized by the use of an elongated cannula structure having a relatively small diameter with a proximal and distal end. The distal end is passed through the surrounding tissue into a body cavity wherein the surgical procedure or examination is to be effected, thus providing a conduit for the insertion of surgical instrumentation. A plurality of cannula structures may be used to allow insertion of a variety of instruments simultaneously during a given procedure. For example, one cannula may provide a conduit for an endoscope for vision and illumination within the operative cavity, while other cannulas may provide conduits for control of specialized surgical instruments designed for performing specific procedural functions.

Surgical procedures often require placing stitches through tissue, a procedure traditionally accomplished by hand. In endoscopic and laparoscopic surgical procedures, suturing internal body tissue presents a particularly challenging task. In such minimally invasive type surgical procedures, suturing must be accomplished through a cannula port that typically averages between five and ten millimeters in diameter. One instrument for facilitating laparoscopic suturing is described in commonly assigned U.S. patent application Ser. No. 08/134,145, filed Oct. 8, 1993, which is incorporated herein by reference. That instrument effects endoscopic suturing by passing a double pointed surgical incision member back and forth through tissue using a unique jaw structure. This jaw structure allows the surgeon to alternately lock the surgical incision member in the first or second jaw. In this manner, tissue can be sutured simply by opening and closing the jaw structure while alternately engaging opposite ends of the surgical incision member.

The shape and design of the surgical incision member is an important aspect of the operation of endoscopic or laparoscopic suturing apparatus. For example, the incision member should be configured to easily penetrate tissue when moved in either longitudinal direction with a minimal incision and should be capable of drawing an attached suture through the incision with little or no additional trauma to the incision. Unlike conventional surgical needles wherein the suture is attached at a proximal end opposite the point and is drawn longitudinally through the incision, the double pointed surgical incision member must be configured to attach the suture at some point intermediate the ends and still avoid trauma to the incision caused by passage of the suture.

SUMMARY

A surgical incision member is provided having a curved body portion defining first and second longitudinal ends, a tissue penetrating portion positioned adjacent the first and second longitudinal ends and suture attachment structure defined in the curved body potion. The curved body portion is preferably of uniform cross-section and further includes first and second apparatus engagement structures for effecting alternate engagement with the jaws of a surgical suturing apparatus. The first and second engagement structures are preferably recesses formed adjacent the first and second longitudinal ends of the curved body portion of the surgical incision member. In one embodiment, an area of the curved body portion adjacent the suture attachment structure is hollowed out or chamfered to form a protective relief for the suture. The suture attachment structure may include a tapered transverse bore configured to facilitate the attachment of a length of suture therein. Preferably, the bore is tapered such that a smallest diameter is adjacent the chamfered area of the curved body portion and a widest diameter is opposite the chamfered area. Alternatively, the suture attachment bore is tapered such that a widest diameter is located adjacent the chamfered area of the body. A taper bore serves to facilitate adhesive attachment of the suture to the curved body portion.

In another alternative embodiment, the body portion includes a bulge along an outer surface portion opposite the chamfered area of the body. This configuration allows the surgical incision member and suture to pass through the body tissue without enlarging the hole in the tissue.

The surgical incision member may further include compression structure which allows the incision member to be crimped or swaged to anchor the suture into the suture attachment structure. In one embodiment at least one protrusion is positioned on an outer surface of the curved body portion adjacent the suture attachment structure. In a particularly preferred embodiment the at least one protrusion is positioned adjacent a transverse bore. The suture is positioned in the bore and the incision member is compressed or swaged so as to force a volume of material into the bore and into contact with the suture therein. Preferably, the at least one protrusion is configured to conform to at least a portion of the circular body. In this configuration, upon compression of the protrusion, material is displaced into the suture attachment aperture while maintaining a substantial uniformly cross-section along the body.

A method is also provided for attaching a suture to a surgical incision member. The method includes providing a surgical incision member having a body portion, tissue penetrating portions adjacent each end of the body portion, and suture attachment structure intermediate the tissue penetrating portions. A surgical suture is inserted at least partially into the suture attachment structure, and the body portion adjacent the suture attachment structure is compressed to crimp the suture to the surgical incision member. This method is particularly effective with an embodiment of the surgical incision member wherein the body portion includes at least one protrusion adjacent the suture attachment structure. Upon compression of the protrusion, material of the body portion is displaced into contact with the suture in the suture attachment structure and the body portion emerges with a substantially uniform cross-section.

BRIEF DESCRIPTION OF THE DRAWINGS

Various embodiments are described hereinbelow with reference to the drawings, wherein:

FIG. 2 is an exploded view of the jaws and the jaw actuating mechanism of the instrument depicted in FIG. 1;

FIG. 3 is a plan view in partial cross-section of the apparatus of FIG. 1, illustrating the jaws in an open position and an incision member secured to the upper jaw;

FIG. 4 is a side view of one embodiment of the surgical incision member illustrating a suture attachment aperture, a suture adhered therein and a chamfered area surrounding the suture attachment aperture;

FIG. 5 is a frontal view in partial cross-section of the surgical incision member of FIG. 4;

FIG. 6 is a side view of the surgical incision member of FIG. 4;

FIG. 7 shows the surgical incision member of FIG. 6 which has been compressed by dies;

FIG. 8 is a cross-sectional view of the body portion of the surgical incision member taken along line 8—8 of FIG. 7;

FIGS. 9 is a side view of an alternative embodiment of the surgical incision member similar to FIG. 4 without the chamfered area;

FIG. 10 is a frontal view in partial cross-section of the surgical incision member of FIG. 9 showing a non-tapered suture attachment aperture;

FIG. 11 is a side view of the surgical incision member of FIG. 9;

FIG. 12 is a side view of the surgical incision member of FIG. 9 after crimping a suture in the suture attachment aperture.

FIGS. 13 is a side view of another alternative embodiment of the surgical incision member similar to FIG. 7, and illustrating protrusions extending outwardly from the body portion;

FIG. 14 is a frontal view in partial cross-section of the surgical incision member of FIG. 13;

FIG. 15 is a side view of the surgical incision member of FIG. 13;

FIG. 16 is a cross-sectional view of the body portion of the surgical incision member taken along line 16—16 of FIG. 15;

FIG. 17 shows the body portion of FIG. 16 positioned between a pair of dies for crimping the suture to the surgical incision member;

FIG. 18 illustrates the body portion of FIG. 16 being crimped on the suture of the surgical incision member;

FIG. 19 shows the body portion of FIG. 16 after crimping and removal of the excess suture lip;

FIG. 20 shows a side view of another alternative embodiment of the surgical incision member;

FIG. 21 is a frontal view in partial cross-section of the surgical incision member of FIG. 20 illustrating a bulge in the side of the body portion;

FIG. 22 is a side view of the surgical incision member of FIG. 20;

DETAILED DESCRIPTION OF PREFERRED EMBODIMENTS

Figure 1:
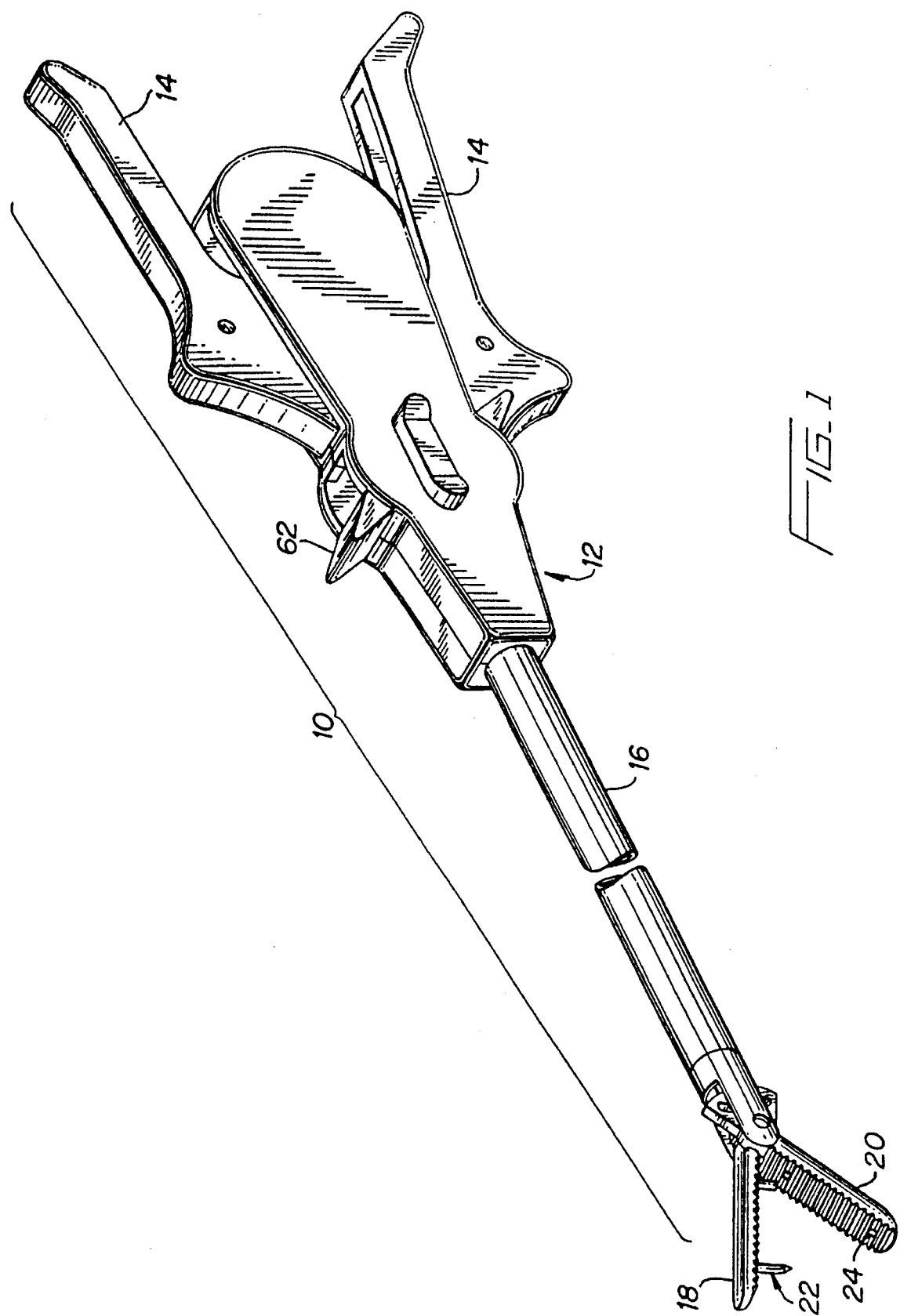
FIG. 1 is a perspective view of an exemplary surgical suturing apparatus in which the surgical incision members may be utilized.

Referring now to the drawings and in particular to FIG. 1, there is shown an exemplary embodiment of a suturing apparatus used in conjunction with the various surgical incision member configurations. The suturing apparatus, generally indicated by reference numeral 10, has a handle housing 12 having a two-armed handle 14, an elongated tubular housing or body portion 16, and two jaws 18 and 20. Handle 14 is used to control the opening and closing of jaws and 20 and is designed to move in the same plane as jaws 18 and 20 to provide an ergonomic advantage. Handle 12 may also be rotatably connected to body portion 16 to provide further ergonomic advantage. This embodiment is particularly well adapted for use in endoscopic or laparoscopic procedures as the tubular housing 16 is preferably dimensioned to be deployable through a tubular cannula structure of between about 5 mm to about 10 mm in internal diameter.

Referring to FIGS. 1, 2 and 3, each jaw is adapted to receive a portion of a surgical incision member 22 in recess 24. When jaws 18 and 20 are closed, the surgical incision member 22 sits in the recess 24 in both jaws. When the jaws are opened, the surgical incision member 22 is retained in one jaw recess 24 depending upon which blade 26 or 28 intersects the surgical incision member 22 through recess 30. As shown in FIG. 3, blade 26, for example, cooperating with upper jaw element 18 has been extended into channel 32 to secure surgical incision member 22 thereto. Alternatively, blade 28 may extend into a corresponding channel in jaw 20 and intersect surgical incision member 22 through recess 34, thus securing surgical incision member 22 in lower jaw dement 20. The movement of the blades to engage the surgical incision member 22 is described in more detail in U.S. Application Serial No. 08/134,145 incorporated by reference hereinabove.

Different embodiments of surgical incision members which may be utilized with the above-described apparatus will now be described. In each embodiment, the surgical incision members 22 include a body portion 22b and tissue penetrating portions, e.g., points 22a, adjacent each end of the body portion 22b. The body portion 22b of the surgical incision member is substantially arcuate in shape and has a radius of curvature which preferably corresponds to the are "R" defined by the motion of the jaws 18 and 20, as shown in FIG. 3. Preferably, the body portion 22b has a substantially uniform circular cross-section with tapered tip portions. However, alternative cross-sectional embodiments and tip configurations are contemplated. For example, the cross-section of the body portion 22b may be square, rectangular, triangular or hollow-ground. Alternative tip configurations include cutting, hollow ground, blunt tapered, spatula, etc. The surgical incision member may be manufactured using known metal injection molding (MIM) techniques. Alternatively, more traditional types of needle forming techniques may be utilized including extruding, cutting, bending, grinding and polishing wire stock.

In the embodiment shown in FIGS. 4–6, the body portion 22b includes apparatus engagement structure shown as recesses 30 and 34 which are configured to alternatively engage blades 26 and 28 of the suturing apparatus. As shown in FIG. 4, recesses 30 and 34 include tapered lead-in portions 30a and 34a which facilitate seating of blades 26 and 28 within each respective recess. Suture attachment structure, in this embodiment shown as aperture 36, is positioned intermediate the pointed ends 22a of the surgical incision member 22, and is preferably positioned adjacent the approximate center of body portion 22b. In FIGS. 4—6, a suture 37 is shown in aperture 36. The aperture 36 is configured to receive a suture 37 and facilitate securement of the suture 37 to the surgical incision member, as will be described below. In this embodiment, a chamfered region 38 is formed in the body portion and protects the suture during penetration of body tissue.

As shown in FIG. 5, suture attachment aperture 36 is preferably tapered, with the widest diameter located at the side of the body portion 22b opposite chamfered region 38 and tapers to the smallest diameter located adjacent the chamfered region 38 of body portion 22b. A suture 37 is inserted through suture aUachment aperture 36, starting from the chamfered region 38, until the tip portion 39 of the suture passes through aperture 36 and suture material occupies the aperture 36. Both monofilament and multifilament sutures are contemplated for use with the surgical incision member disclosed herein. Where a multifilament suture is to be used, one end thereof is tipped to facilitate insertion of the suture into the suture attachment structure. Where monofilament sutures are to be used, no such tipping is required. Where an adhesive is used to attach the suture to the incision member, the adhesive is applied from one or both ends of aperture 36 and wicks into the suture so as to surround the suture and fill suture attachment aperture 36. Suitable adhesives include medical grade cyanoacrylate glue, epoxy cements and other medically acceptable adhesives.

Alternatively, as shown in FIGS. 7 and 8, the suture may be attached to the surgical incision member by crimping or swaging the body portion 22b adjacent suture attachment aperture 36 with one or more dies so as to compress the body portion into the aperture 36 and crimp the suture into the aperture. Once the suture is attached any excess portion of the suture extending through the needle is cut off 37 flush with the surface of the body portion 22b to minimize trauma to tissue. The balance of the suture extends from the chamfered area of the surgical incision member as shown in FIG. 5.

Referring now to the embodiment of FIGS. 9–11, the surgical incision member 22 shown is substantially similar to the embodiment of FIGS. 4–6. However, in this embodiment the chamfered area is omitted and the non-tapered suture attachment aperture 36 extends through the body portion 22b as shown in FIG. 10. Attachment of the suture to the surgical incision member may be accomplished using either technique described above. FIG. 12 shows a surgical incision member in accordance with FIG. 9 wherein the suture 37 has been crimped therein.

Referring now to FIGS. 13–16, another embodiment of the surgical incision member is shown. In this embodiment, the body portion 22b is also arcuate in shape and has a radius of curvature approximately equal to the arc "R" defined by the motion of the jaws 18 and 20 of the suturing apparatus 10, as described above. Suture attachment aperture 40 extends through the body portion 22b and is positioned intermediate points 22a, preferably at the approximate center of the surgical incision member, as shown in FIG. 14. Protrusions 42 and 44 extend outwardly from the body portion 22b adjacent suture attachment aperture 40, as shown in FIGS. 13–15. The surgical incision members according FIGS. 13–15 preferably have a substantially circular configuration and the protrusions are configured to conform to that circular configuration, as shown in FIG. 16.

Suture 46, shown in FIGS. 17–19 is preferably a tipped multifilament suture 46 having a relatively rigid tip portion 47 to facilitate insertion into suture attachment aperture 40 and a soft, manipulable suture body portion 49. Suture attachment is effected as follows. The tip portion 47 of suture 46 is inserted through one opening of the suture attachment aperture 40 until the entire tip portion 47 extends from the other opening of aperture 40. A pair of dies 50 and 52 impact the protrusions 42 and 44, shown in FIGS. 17–18, to crimp the body portion 22b and attach the suture body 49 thereto by compression force. Preferably, each die 50 and 52 has a curved surface 54 and 56 respectively, with a radius of curvature corresponding to the radius of curvature of circular body portion 22b. In this configuration, when the dies impact protrusions 42 and 44, material of the body portion is compressed toward the center of aperture 40 and the volume of material of each protrusion 42 and 44 is displaced inwardly to occupy the portion of the body which has been deformed to engage the suture. As a result, a substantially uniform cross-section is maintained throughout the length of the body portion 22b, including the suture attachment region. Maintaining the uniform circular cross-section along the length of the surgical incision member minimizes the force required to pass through tissue and also minimizes trauma to the tissue by minimizing the incision size. FIG. 19 illustrates the cross-section of the suture attachment region after dies 50 and 52 have impacted the surgical incision member and the portion 47 of the suture 46 is severed so that the suture within the suture attachment aperture 40 is flush with the surface of body portion 22b. Advantageously the soft, manipulable suture body portion 49 facilitates easy handling of the surgical incision member and permits smooth passage of the suture through the incision.

Another alternative embodiment of the suture incision member is shown in FIGS. 20–22. In this embodiment, the body portion 22b includes the chamfered area 38 and a flared (or tapered) suture attachment aperture 58. In addition, the body portion 22b includes a bulge 60 extending outwardly from the side of the body portion opposite chamfered region 38. The bulge configuration may allow the surgical incision member and suture to pass through tissue without enlarging the hole in the tissue.

Referring to FIG. 21, to attach the suture 46 to the surgical incision member 22, the tipped portion of the suture is inserted into aperture 58 at the side of the body portion having the chamfered area. The tipped portion is passed through the aperture until it extends from the bulged side of the body portion. A suitable medically acceptable adhesive, such as a medical grade cyanoacrylate glue, is deposited into aperture 58. Similar to the above described embodiments, once the suture is attached, the tipped portion of the suture is severed or cut off flush with the surface of the body portion to minimize trauma to the tissue.

Figure 23:
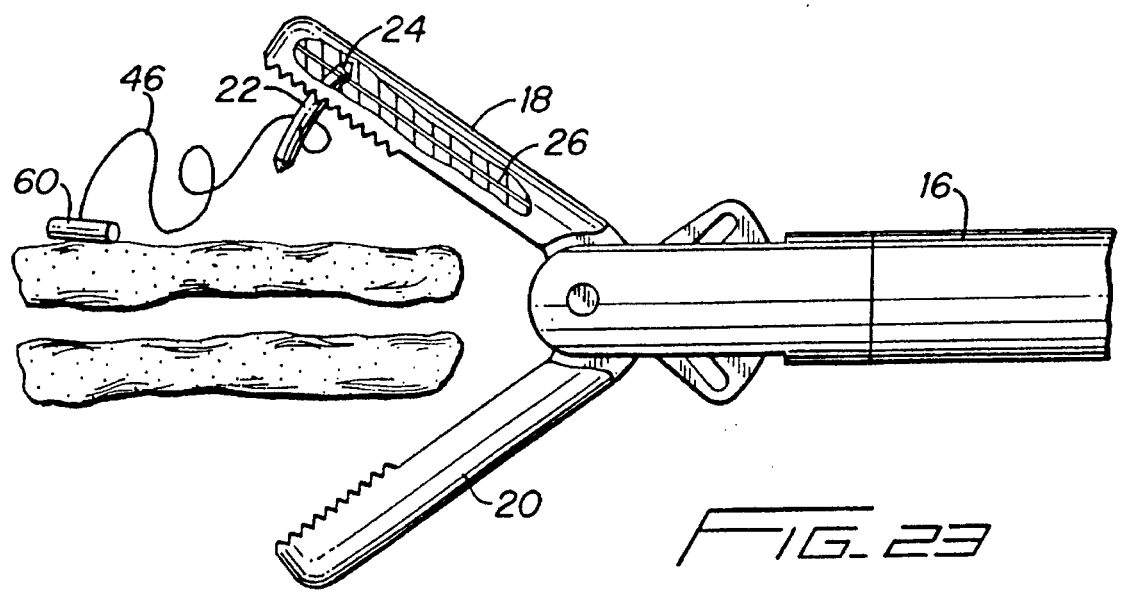
FIG. 23 shows a side view in partial cross-section of a suturing apparatus loaded with a surgical incision member in position adjacent tissue to be sutured.
Figure 24:
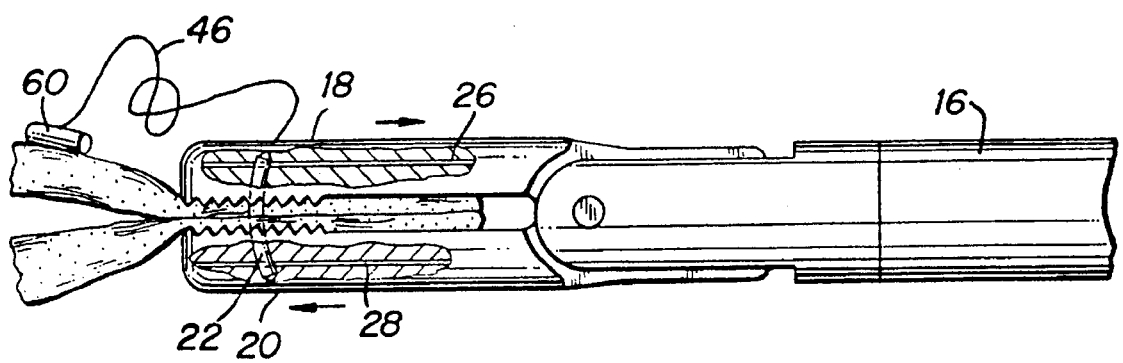
FIG. 24 shows the surgical incision member being passed through the tissue by the suturing apparatus.
Figure 25:
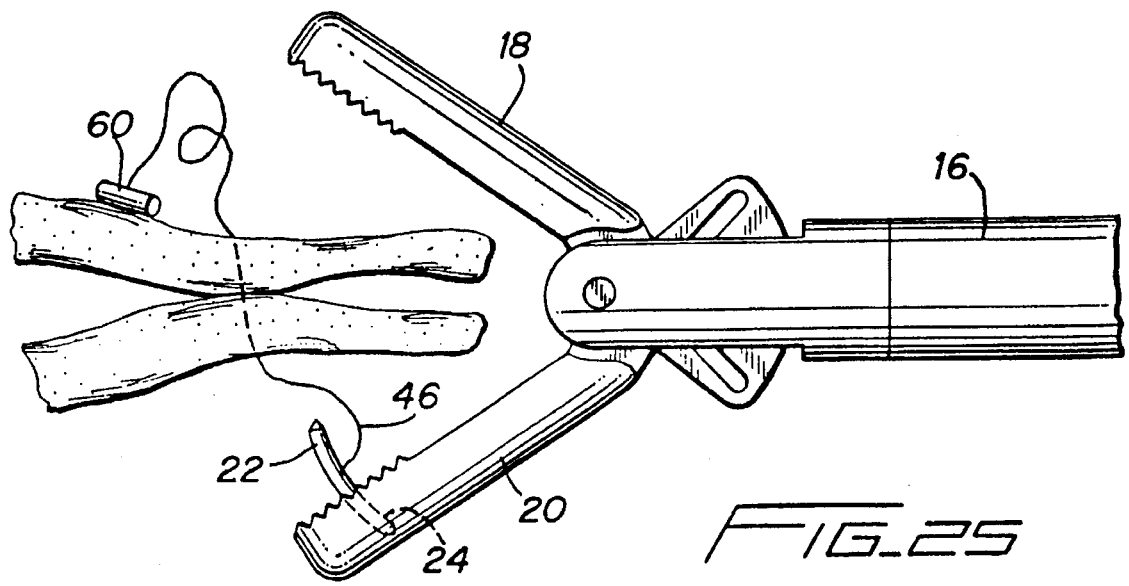
FIG. 25 shows the surgical incision member being drawn out of the tissue to implant a suture therein.

Referring to FIGS. 23, 24 and 25; to operate the suturing apparatus 10, the open jaws 18 and 20 mounting a surgical incision member are positioned around the tissue to be sutured. As shown in FIG. 22, the surgical incision member 22 is initially secured to upper jaw 18 by blade 26. Handles 14 are approximated toward each other, closing the jaws 18 and 20 around the tissue so that the surgical incision member 22 penetrates the tissue and is guided into recess 24 in jaw 20. To secure the surgical incision member 22 to jaw 20, wheel 62, shown in FIG. 1, is rotated so that blade 26 retracts from recess 30 in the surgical incision member 22, and blade 28 slides into engagement with recess 34. The jaws are then opened, as shown in FIG. 24, and the suture is pulled through the tissue. The surgical incision member is ready to make another stitch by repeating the above described steps. As shown in the Figures, the suture 46 includes an anchor 60 attached at one end to facilitate attachment in tissue.

It will be understood that various modifications can be made to the embodiments disclosed herein. For example, various sizes of the surgical incision members are contemplated, as well as surgical incision members having various types of cross-sections. Apertures as used herein are not limited to through bores and include blind holes. Therefore, the above description should not be construed as limiting, but merely as exemplifications of preferred embodiments. Those skilled in the art will envision other modifications within the scope and spirit of the claims appended hereto.

What is claimed is:

1. A surgical incision member for remote suturing of tissue comprising:
 a curved body portion of substantially uniform cross-section defining first and second longitudinal ends;
 tissue penetrating portions adjacent the first and second longitudinal ends;
 suture attachment structure defined in the curved body portion for receiving a portion of a suture to be attached to the surgical incision member; and
 a chamfer formed in the body portion adjacent the suture attachment structure, wherein the body portion includes a bulge along an outer surface opposite the body chamfer.

2. A surgical incision member comprising:
 a curved body portion;
 tissue penetrating portions adjacent each end of the body;
 a suture attachment aperture intermediate the tissue penetrating portions; and
 at least one protrusion intermediate the tissue penetrating portion andextending from the body portion adjacent the suture attachment aperture.

3. A surgical incision member as in claim 2, further comprising at least one recess along an outer surface of the body portion, the outer surface corresponding to one side of the body portion in which the suture attachment aperture extends and the at least one recess is transverse to a center axis of the aperture.

4. A surgical incision member as in claim 2, wherein the body is substantially circular in cross-section and the at least one protrusion is configured to conform to at least a portion of the circular body, such that upon compression of the at least on protrusion by at least one die a portion of the body portion is displaced into the suture attachment aperture to yield a substantially uniform cross-section along the body portion.

5. A surgical incision member as in claim 4, further comprising a suture affixed in the suture attachment aperture.

6. A surgical incision member as in claim 2, further comprising a chamfer formed in the body portion adjacent the suture attachment aperture.

7. A surgical incision member as in claim 2, further comprising apparatus engagement structure formed in the body portion adjacent the tissue penetrating portions.

8. A surgical incision member as in claim 7 wherein the apparatus engagement structure comprises a substantially transverse recess offset from a center longitudinal axis of the body portion.

9. A surgical incision member as in claim 2 wherein the tissue penetrating portions comprise points formed at each longitudinal end of the body portion.

10. A method for attaching a suture to a surgical incision member comprising the steps of:
 providing a surgical incision member having a curved body portion, a tissue penetrating portion adjacent each longitudinal end of the body portion and suture attachment structure intermediate the tissue penetration portions;
 inserting a portion of a suture into the suture attachment structure; and
 permanently affixing the suture in the suture attachment structure wherein the suture attachment structure is an aperture and the step of inserting a portion of the suture includes inserting a portion of the suture through the aperture until the portion extends out the aperture and removing the portion which extends out of the aperture flush with the body portion after the suture is permanently affixed in the aperture.

11. The method as in claim 10 wherein the suture is a tipped multifilament suture and the portion of the suture is a tipped portion of the multifilament suture wherein the tipped portion is inserted through the aperture, the suture is affixed to the body portion and at least a part of the tipped portion is removed flush with the body portion.

12. A method for attaching a suture to a surgical incision member comprising:
 providing a surgical incision member having a body portion, a tissue penetration portion adjacent each end of the body portion, a suture attachment aperture intermediate the tissue penetrating portions and at least one protrusion extending from the body portion adjacent the suture attachment aperture;
 inserting a suture at least partially into the suture attachment aperture; and
 compressing the at least one protrusion such that a portion of the body portion is displaced radically inwardly into the suture attachment aperture to crimp the suture so as to secure the suture to the body portion.

13. The method according to claim 12, wherein the step of compressing includes compressing the at least one protrusion to occupy the displaced portion of the body to yield a uniform cross-section of the body.

14. The method as in claim 12 further comprising the steps of inserting the suture through the suture aperture until a portion of the suture extends from the body portion and removing the suture portion which extends from the body portion flush with the body portion after the suture has been affixed in the aperture.

15. The method as in claim 14 wherein the suture is a multifilament suture.

16. The method as in claim 15 wherein the suture is a tipped multifilament suture and at least a portion of the tipped multifilament suture is removed flush with the body portion.

* * * * *